(12) United States Patent
Verheem (10) Patent No.: US 11,666,776 B2
(45) Date of Patent: Jun. 6, 2023

(54) LIGHT TREATMENT DEVICE

(71) Applicant: Johann Verheem, Carlsbad, CA (US)

(72) Inventor: Johann Verheem, Carlsbad, CA (US)

( * ) Notice: Subject to any disclaimer, the term of this patent is extended or adjusted under 35 U.S.C. 154(b) by 0 days.

(21) Appl. No.: 17/029,944

(22) Filed: Sep. 23, 2020

(65) Prior Publication Data

US 2021/0001148 A1     Jan. 7, 2021

Related U.S. Application Data

(63) Continuation-in-part of application No. 16/819,016, filed on Mar. 13, 2020.

(60) Provisional application No. 63/010,681, filed on Apr. 15, 2020, provisional application No. 63/008,866, filed on Apr. 13, 2020, provisional application No.
(Continued)

(51) Int. Cl.
*A61N 5/06* (2006.01)
*A61M 37/00* (2006.01)

(52) U.S. Cl.
CPC .......... *A61N 5/0616* (2013.01); *A61M 37/00* (2013.01); *A61N 2005/063* (2013.01); *A61N 2005/0629* (2013.01); *A61N 2005/0632* (2013.01); *A61N 2005/0644* (2013.01)

(58) Field of Classification Search
CPC .......... A61N 5/0616; A61N 2005/0629; A61N 2005/063; A61N 2005/0632; A61N 2005/0644; A61N 2005/0652; A61M 35/003; A61M 37/00
See application file for complete search history.

(56) References Cited

U.S. PATENT DOCUMENTS

| 5,320,617 | A  | 6/1994 | Leach |
| 9,101,524 | B2 | 8/2015 | Aghion |
| 9,272,141 | B2 | 3/2016 | Nichols |

(Continued)

FOREIGN PATENT DOCUMENTS

| JP | 2012-75543 | A |   | 4/2012 |
| JP | 2012075543 | A | * | 4/2012 |

OTHER PUBLICATIONS

PCT International Search Report for PCT/US2021/022044, dated Jun. 22, 2021.
PCT Written Opinion for PCT/US2021/022044, dated Jun. 22, 2021.

*Primary Examiner* — Mallika D Fairchild
*Assistant Examiner* — Shreya Anjaria
(74) *Attorney, Agent, or Firm* — Rosenthal IP Law; Larry Rosenthal (57) ABSTRACT

A handheld light treatment device that aims to provide a wide variety of uses in personal care and household cleaning. The device contains a panel with light sources positioned behind a translucent or transparent head plate, to which is attachable an applicator disc and, optionally, applicator disc attachments with selected functionalities. The light panel shines light of different frequencies that may be useful for cleaning and sanitizing various surfaces. The applicator disc and applicator disc attachments have a substantially translucent or transparent base, allowing light from the light sources to shine through the head plate as well as applicator disc and applicator disc attachment, and the applicator disc to rotate while the light panel remains fixed. The applicator disc and applicator disc attachments may have bristles or other surface elements to facilitate cleaning or other uses, and the device may dispense an ingredient.

16 Claims, 8 Drawing Sheets

Related U.S. Application Data

62/878,150, filed on Jul. 24, 2019, provisional application No. 62/818,180, filed on Mar. 14, 2019.

(56) References Cited

U.S. PATENT DOCUMENTS

| | | | |
|---|---|---|---|
| 9,554,963 B2 | 1/2017 | Pilcher | |
| 9,585,687 B2 | 3/2017 | Tenenbaum | |
| 2004/0147984 A1* | 7/2004 | Altshuler | A46B 13/023 607/88 |
| 2005/0113725 A1* | 5/2005 | Masuda | A61H 23/0263 601/72 |
| 2007/0198004 A1* | 8/2007 | Altshuler | A61N 5/0616 606/9 |
| 2008/0243039 A1* | 10/2008 | Rhoades | A61N 5/0616 601/72 |
| 2009/0240310 A1* | 9/2009 | Kennedy | A61N 5/0616 607/89 |
| 2011/0184499 A1* | 7/2011 | Radi | A61N 7/00 607/88 |
| 2014/0135798 A1* | 5/2014 | David | A61B 17/3205 606/131 |
| 2014/0222026 A1* | 8/2014 | Tenenbaum | A61N 7/00 606/131 |
| 2014/0296772 A1 | 10/2014 | Duquet et al. | |
| 2015/0327653 A1 | 11/2015 | Decaux et al. | |
| 2018/0071547 A1 | 3/2018 | Decaux et al. | |
| 2018/0325328 A1 | 11/2018 | Wright | |

\* cited by examiner

LIGHT TREATMENT DEVICE

CROSS-REFERENCE TO RELATED APPLICATIONS

This application claims priority to U.S. Provisional Patent Application No. 62/878,150 entitled "Device for Treating Skin" and filed on Jul. 24, 2019, U.S. Provisional Patent Application No. 63/008,866 entitled "Skin and Surface Brush" and filed on Apr. 13, 2020, and U.S. Provisional Patent Application No. 63/010,681 entitled "Cleansing Device with Light" and filed on Apr. 15, 2020, and is a continuation-in-part of U.S. Non-Provisional patent application Ser. No. 16/819,016 filed on Mar. 13, 2020, which claims priority to U.S. Provisional Patent Application No. 62/878,150 entitled "Device for Treating Skin" and filed on Jul. 24, 2019, and U.S. Provisional Patent Application No. 62/818,180 entitled "Device for cleaning and applying skin care ingredients" and filed Mar. 14, 2019.

BACKGROUND

Cleansing, sanitizing and treating the skin is a common part of many people's daily routines. Many different types of skin creams, lotions, soaps and medications are applied to the skin in order to treat or prevent aging, affect wrinkles, reduce discoloration, pigmentation and age spots and eliminate medical skin conditions such as acne and sanitize or cleanse the skin from contaminants, viruses and bacteria. Skin care and hair care can also include treatment of the human scalp. In addition, nails are often treated with creams, lotions and decorated with paints and other soluble ingredients.

Applying physical force through brushing, scrubbing, wiping and massaging the skin aim to clean and sanitize the surface of the skin, remove dead skin cells and impurities and stimulate the skin to produce new skin cells and repair itself. Adding lotion, creams and medications to a skin care regiment enhances the beneficial effect of physically cleaning and massaging the skin.

Various forms of light have been used to enhance sanitization of surfaces and to treat human skin, hair and nails. Light of different frequencies are emitted from a light source on the skin which can support production of collagen, increase blood flow, kill viruses and bacteria and reduce inflammation. These light frequencies include but are not limited to ultraviolet light, near infrared light, infrared light and blue light. Phototherapy can also be used outside of the field of skin care to provide cleaning and sanitization benefits.

Hot and cold materials placed on the skin have also been demonstrated to have medical, cosmetic and therapeutic benefits. In addition, vibration from an electric source and sonic waves from an electrical device have been demonstrated to have medical, cosmetic and therapeutic benefits.

BRIEF DESCRIPTION OF THE DRAWINGS

Embodiments of the present technology will be described and explained through the use of the accompanying drawings. The same reference numbers in different drawings may identify the same or similar elements.

The drawings, some components and/or operations can be separated into different blocks or combined into a single block when discussing some embodiments of the present technology. Moreover, while the technology is amenable to various modifications and alternative forms, specific embodiments have been shown by way of example in the drawings and are described in detail below. The intention, however, is not to limit the technology to the particular embodiments described herein. On the contrary, the technology is intended to cover all modifications, equivalents, and alternatives falling within the scope of the technology as defined by the appended claims.

DETAILED DESCRIPTION

The embodiments set forth below represent the necessary information to enable those skilled in the art to practice the embodiments and illustrate the best mode of practicing the embodiments. Upon reading the following description in light of the accompanying figures, those skilled in the art will understand the concepts of the disclosure and will recognize applications of these concepts that are not particularly addressed herein. It should be understood that these concepts and applications fall within the scope of the disclosure and the accompanying embodiments.

The purpose of the terminology used herein is only for describing embodiments and is not intended to limit the scope of the disclosure. Unless defined otherwise, all terms of art, notations and other scientific terms or terminology used herein have the same meaning as is commonly understood by one of ordinary skill in the art to which this disclosure belongs. In some cases, terms with commonly understood meanings are defined herein for clarity and/or for ready reference, and the inclusion of such definitions herein should not necessarily be construed to represent a substantial difference over what is generally understood in the art. All patents, applications, published applications and other publications referred to herein are incorporated by reference in their entirety. If a definition set forth in this section is contrary to or otherwise inconsistent with a definition set forth in the patents, application, published applications and other publications that are herein incorporated by reference, the definition set forth in this section prevails over the definition that is incorporated herein by reference.

Unless otherwise specified herein, the features of the presently disclosed solution may be economically molded or assembled by using one or more distinct parts and associated components which may be assembled together for removable or integral application.

Where context permits, words using singular or plural form may also include the plural or singular form, respectively. As used herein, "a" or "an" means "at least one" or "one or more." As used herein, the term "user", "subject", "end-user" or the like is not limited to a specific entity or person. For example, the term "user" may refer to a person who uses the systems and methods described herein, and frequently may be a technician. However, this term is not limited to end users or technicians and thus encompasses a variety of persons or entities who can use the disclosed systems and methods.

Figure 1:
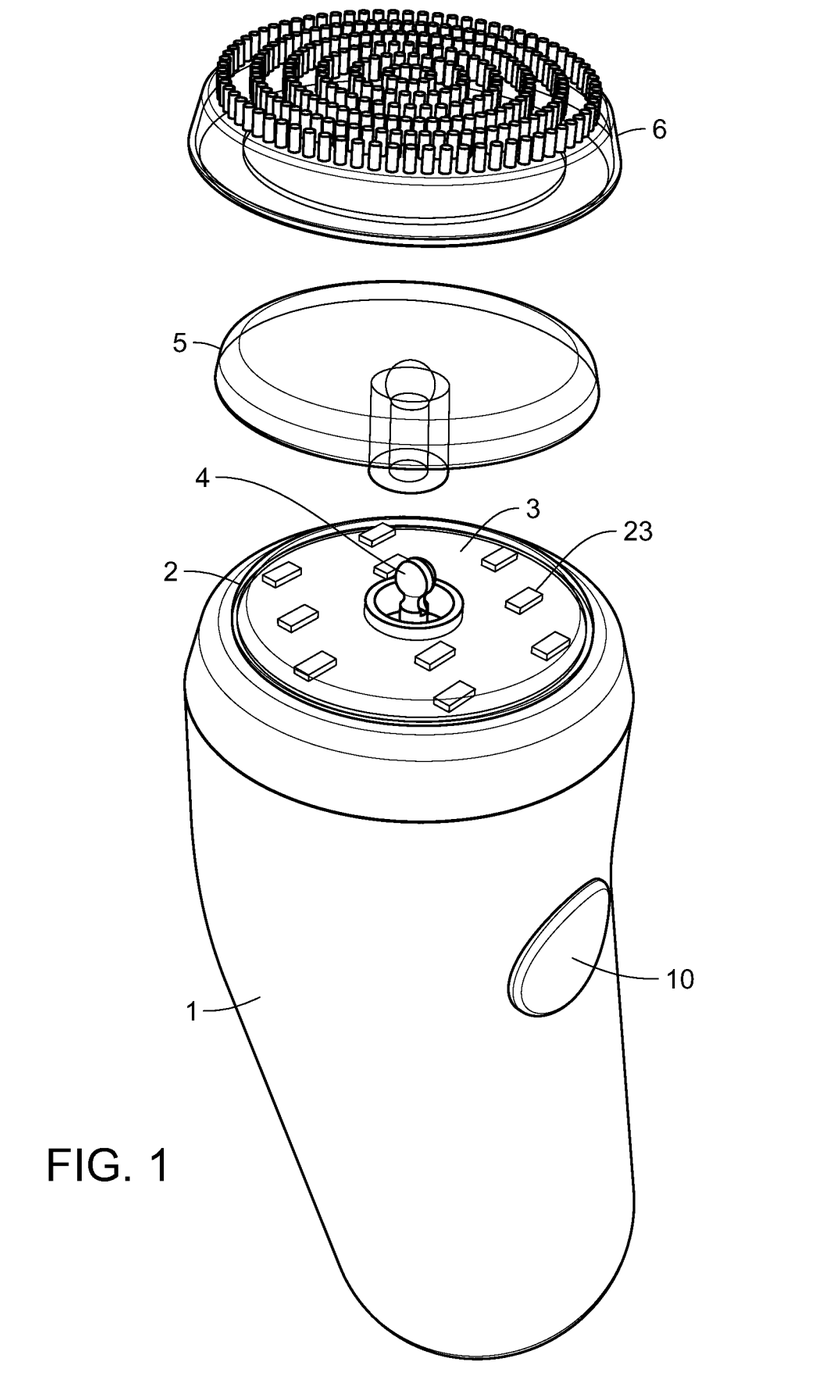
FIG. 1 is a partially exploded perspective view of a representative embodiment of the device.

FIG. 1 is a partially exploded perspective view of a representative embodiment of the light therapy device when viewed from the head of the device, which comprises a housing [1] and, at one end of the housing [1], a solid, transparent or translucent head plate [2] integral with the housing. The housing [1] is essentially the handle of the device, and to that end can be sized for holding in the hand, such that the head of the device can be controlled, pointed and directed as intended by a user. The housing may comprise a handle or grip in a wide variety of sizes and shapes without limitation. Secured within housing [1] behind transparent or translucent head plate [2] is a panel [3] comprising one or more light sources [23] whereby the one or more light sources [23] can shine through the head plate [2] to provide phototherapy benefits.

Figure 2:
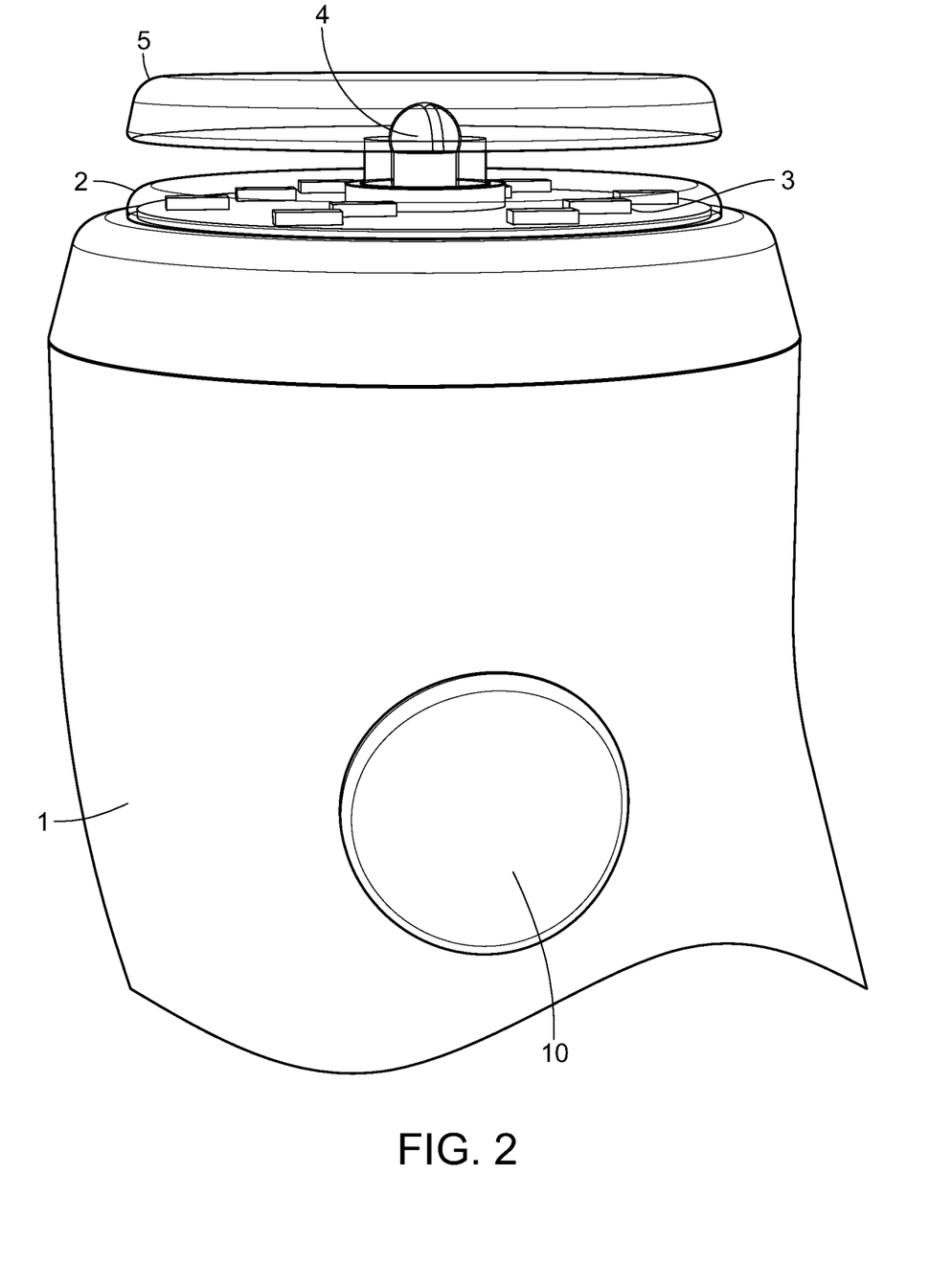
FIG. 2 is a front perspective view of a representative embodiment of the device.
Figure 3:
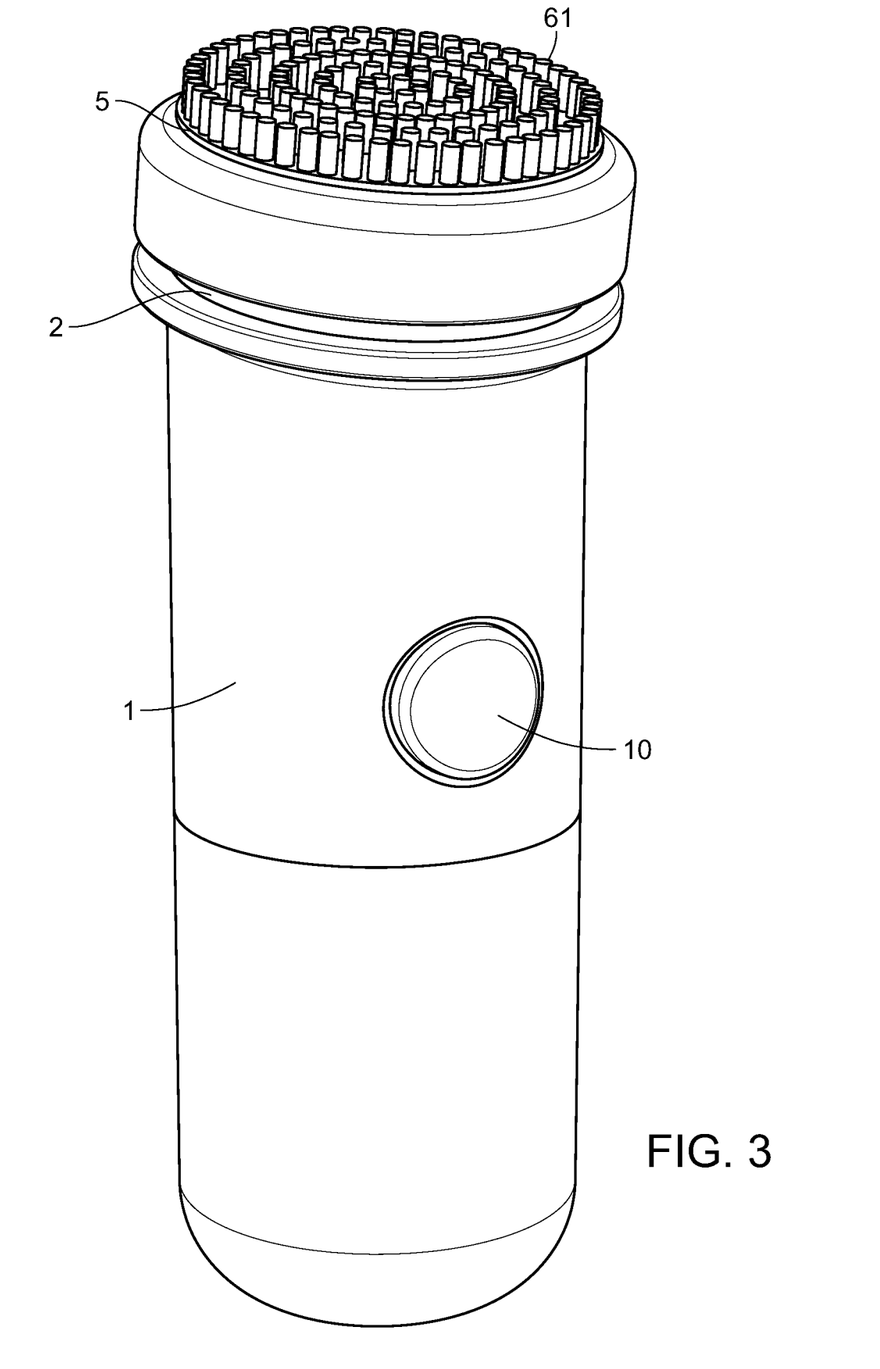
FIG. 3 is a front perspective view of a representative embodiment of the device.

FIG. 2 is a side perspective view of a representative embodiment of the device. An applicator disc [5] is attachable to the device over the head plate [2], the applicator disc [5] being substantially transparent or translucent such that the light sources when shining through the head plate [2] also shine through the applicator disc [5]. The applicator disc [5] may be a fully transparent or translucent disc, comprising transparent or translucent surface elements, or it may comprise a base of one or more transparent or translucent sections while surface elements such as brush bristles [61] are non-transparent or non-translucent. FIG. 3 is a perspective view of a representative embodiment of the light therapy device with bristles [61] incorporated into an applicator disc having a transparent or translucent base [5].

Figure 4:
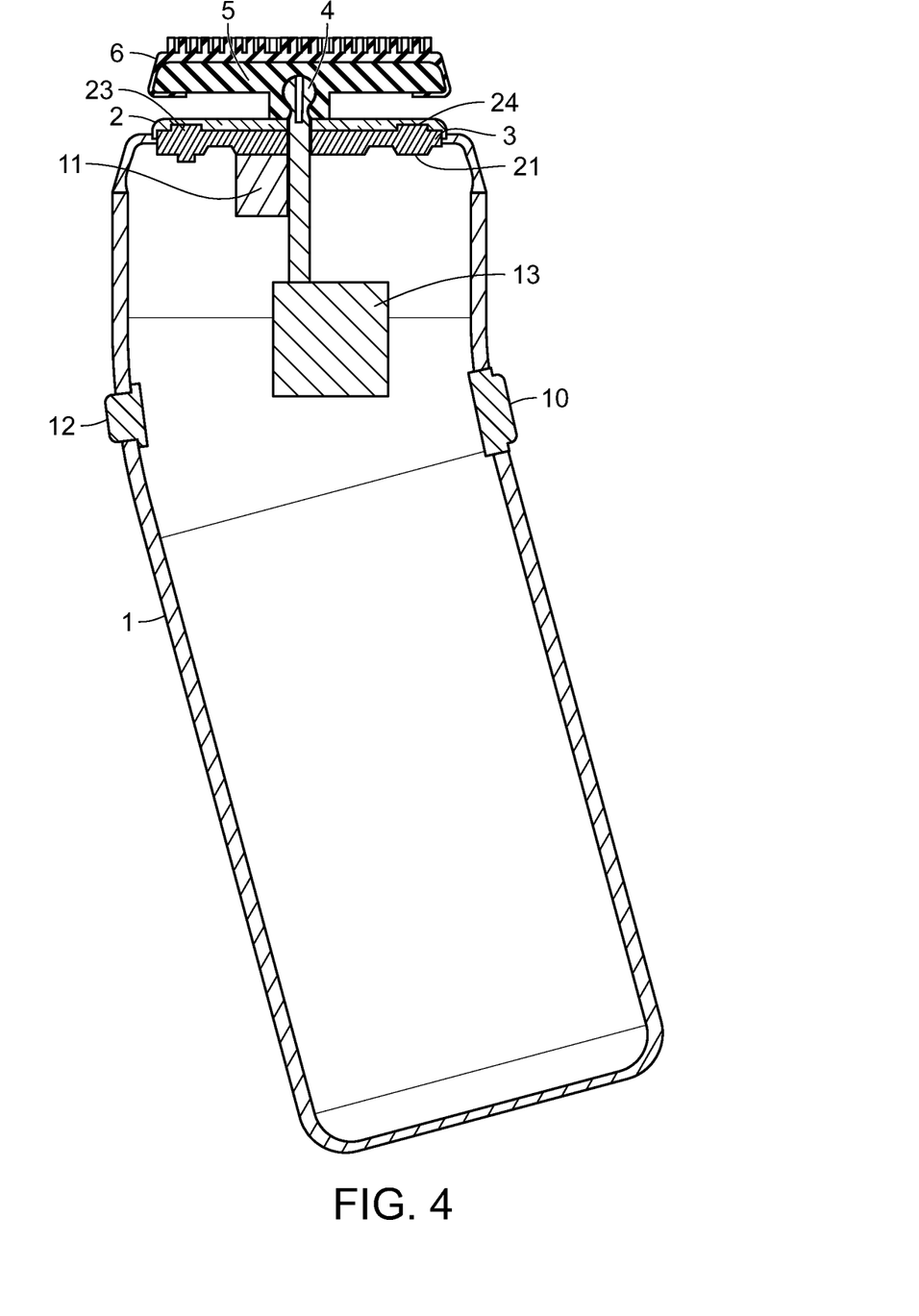
FIG. 4 is a cross-sectional view of a representative embodiment of the device.

FIG. 4 is a cross-sectional view of a representative embodiment of the light therapy device. Applicator disc [5] may be operatively coupled to a motor [11] secured within housing [1] such that applicator disc [5] is operable to rotate while the panel [3] with one or more light sources [23] remains fixed. For example, applicator disc [5] may be attachable to one end of a shaft [4] operatively coupled to motor [11] within the device. The shaft [4] may transect the head plate [2], for instance protruding through an aperture in the head plate [2]. By rotating the shaft, applicator disc [5] may rotate while the rest of the device, including panel [3] including light sources [23], and head plate [2], remain fixed. The shaft may create a space between applicator disc [5] and head plate [2], facilitating access and movability to applicator disc [5]. For instance, applicator disc can be made disposable, or can be configured to accept disposable attachments or attachments with different types of operating surfaces.

Figure 7:
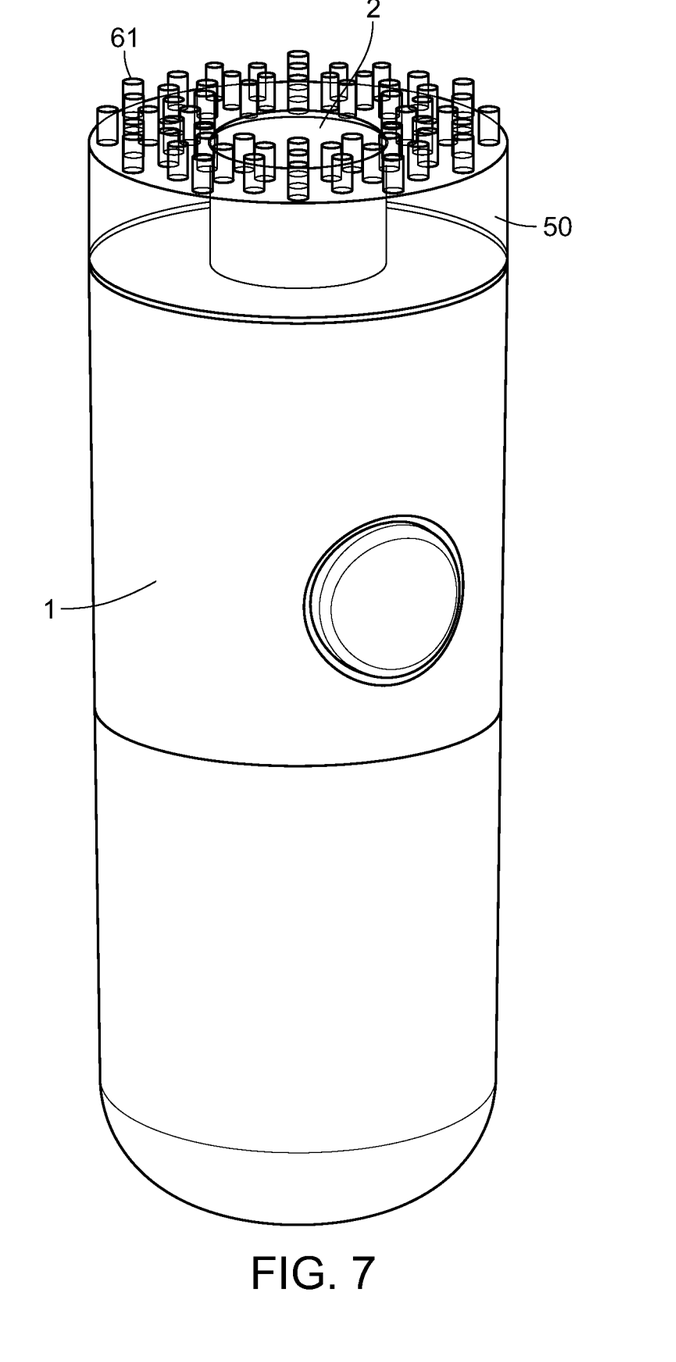
FIG. 7 is a front perspective view of a representative embodiment of the device.

FIG. 7 is a side perspective view of a representative embodiment of the light therapy device. As another example, the applicator disc may be an attachment that surrounds transparent or translucent head plate [2], wherein the applicator attachment [50] attaches to a part of the housing [1] that rotates while head plate [2], and panel [3] and its light sources [23], remain fixed. For example, said applicator attachment [50] may comprise a transparent or translucent disc section over the transparent or translucent head plate [2], or it may surround the transparent or translucent head plate [2].

In this manner, the light therapy device can be used by holding the housing [1] of the device and moving the device across the skin, hair, scalp or nails, or other applied surface in a manner where applicator disc [5] is touching or facing said skin, hair, scalp or nails, or other applied surface. The light sources mounted on the panel [3] behind the applicator disc [5] shine through to provide phototherapy benefits while the device is applied. For instance, the device may be applied during facial cleansing to clean the skin while simultaneously providing phototherapy benefits. It will be noted that the device may have other applications other than to skin, as light therapy can have broad applications. As another example, the device can be used with UV light to sterilize dishes while washing. The device may be used without attaching the applicator disc, for instance when light is desired to be applied without the additional effects of the applicator disc. The entire device may be waterproof.

Figure 6A:
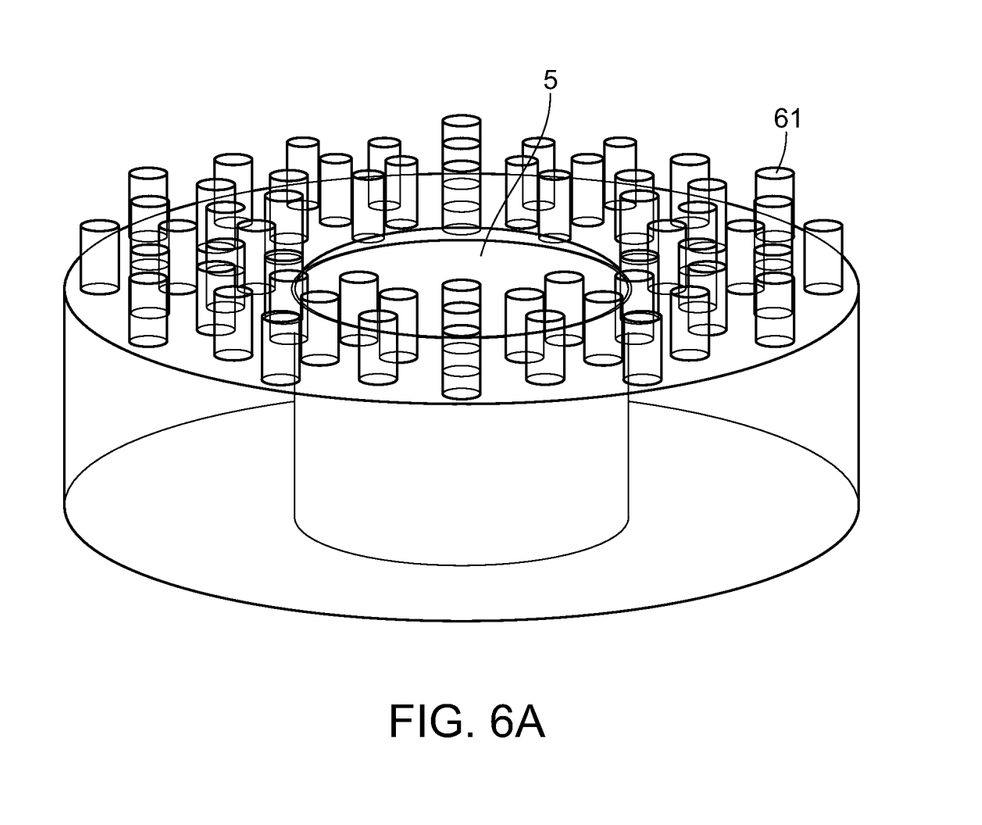
FIG. 6A is a plan view of a representative embodiment of the translucent disc.
Figure 6B:
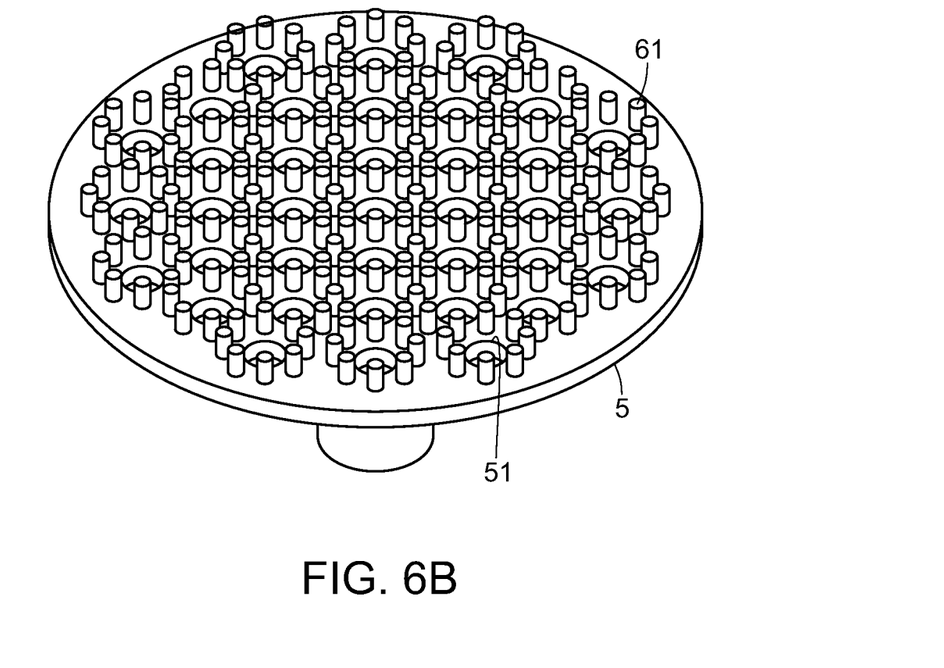
FIG. 6B is a plan view of a representative embodiment of the translucent disc.
Figure 6C:
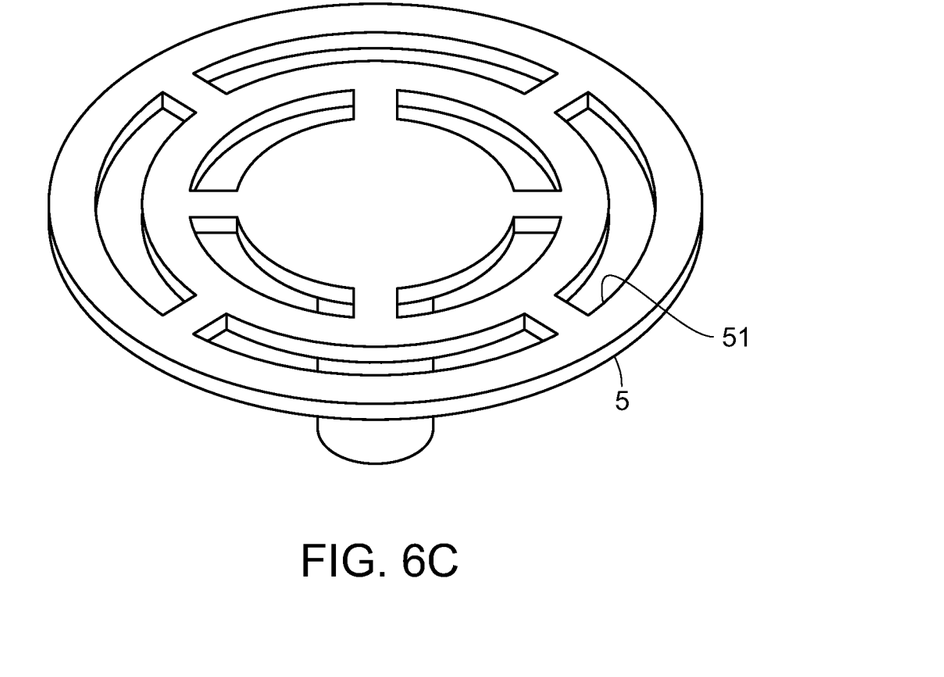
FIG. 6C is a plan view of a representative embodiment of the translucent disc.

Applicator disc [5] may incorporate a variety of surface elements such as a brush with hair or tentacles, pads, abrasive material such as sand paper, silicone or rubber surfaces, metal, glass, rolling balls made from rigid materials and other constrictions where the surface interacts with the skin in a beneficial way. These surface elements can be non-transparent and non-translucent so long as applicator disc [5] comprises one or more transparent or translucent sections [51] in its base through which light may shine. For instance, the entire base of applicator disc [5] may transparent or translucent, and it may incorporate opaque bristles or other surface elements, or it may incorporate transparent or translucent bristles or other surface elements. The applicator disc [5] may comprise non-transparent or non-translucent surface elements interspersed between transparent or translucent sections of its base. 6A-6C. FIGS. 6A-6C are top perspective views showing such examples of configurations of applicator disc [5].

Surface elements may be attached to applicator disc [5] by means of a disc cover [6], for instance a disposable cover, also substantially transparent or translucent, whereby light from panel [3] can shine through transparent or translucent head plate [2], transparent or translucent applicator disc [5], and disc cover [6]. The disc cover [6] may comprise an abrasive or non-abrasive cleaning pad or wipe. The disc cover [6] may be made attachable by various attachment means such as snap in or snap on, screw connection, magnetic, adhesive, hook and loop fasteners, etc. . . . . The disc cover [6] may be comprised of flexible or inflexible materials. For instance, with reference to FIG. 1 or 3, disc cover [6] may comprise a flexible silicone cover with a lip that secures around the edge of the applicator disc [5], or an inflexible cover that snaps onto or screws over applicator disc [5].

Similar to applicator disc [5], disc cover [6] may comprise a base of one or more transparent or translucent sections such that light can emanate through head plate [2], applicator disc [5], and through said transparent or translucent sections of disc cover [6]. For example, entire disc cover [6] may be a transparent or translucent flexible silicone cover, comprising transparent or non-transparent bristles, or it may comprise non-transparent or non-translucent surface elements interspersed between transparent or translucent sections of its base, analogous to examples in FIGS. 6A-6C.

The device may be operable to dispense an ingredient so that simultaneously, the light reaches the ingredient as well as the user's skin, hair, scalp or nails, or other applied surface. The light can impact the ingredient, so that chemical processes or alterations in the ingredient are activated. The light source can also impact the user's skin, scalp or nails, by increasing blood flow, in the case of certain red frequencies of light, or by killing bacteria or viruses on the surface of the skin, such is the case with certain blue frequencies of light. The light can also act as a source of heat that melts the ingredient when dispensed through the applicator or that heats up either the ingredient, the skin, hair or nails of the user or both ingredient ad housing part of the user in order to provide therapeutic or cosmetic benefits.

For example, the housing [1] may incorporate a chamber [13] to hold said ingredient, which may be transmitted through shaft [4] and/or through openings in applicator disc [5] and optional disc cover [6]. Applicator disc [5] and/or disc cover [6] may comprise a chamber into which various elements such as hot or cold gel containers or ice can be inserted, for instance, such that the surface covering can provide temperature specific benefits to the skin, or said chamber may contain liquid ingredients such as skin creams, lotions, medication, sanitizers and soaps that are dispensed through an opening to the skin of the user. Applicator disc [5] and/or disc cover [6] can be made from a material that retains heat or cold. Applicator disc [5] or disc cover [6] may be impregnated with a material so that it deposits the ingredient to the surface being cleaned.

Figure 5:
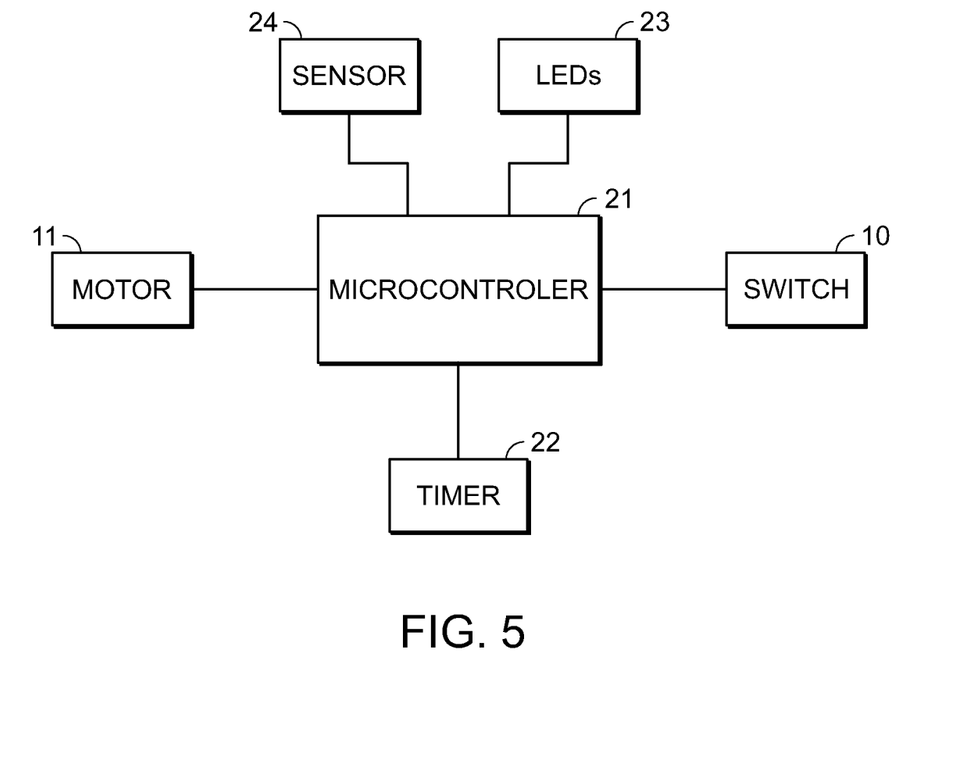
FIG. 5 is a block diagram of representative elements for operating the device.

The panel [3] may be an electronic circuit board comprising one or more light emitting diodes (LEDs) [23] on its outer surface, i.e. the surface facing the translucent head plate [2]. FIG. 5 is a block diagram of elements for operating the device. For example, the panel [3] may comprise a microcontroller [21] for operating LEDs [23]. The microcontroller [21] may be programmable to control the frequency of lights emitted by the LEDs [23], since different frequencies of light have different effects in the treatment of various conditions. For instance, blue light frequencies are known as an effective treatment for acne, while infrared frequencies are known to stimulate blood circulation. It should be noted that the device is readily adaptable to different uses other than skin treatments, for example, light sources [23] may emit UV light which may be used on various articles for sterilization.

The transparent or translucent head plate [2] is assembled integral with the housing of the device and may be planar or it may have other surface topology. The translucent or transparent head plate [2] and/or translucent or transparent applicator disc [5] may integrate lenses to further focus and/or direct the lights.

The panel [3] may additionally comprise a sensor [24], for example on its outer surface, such that the light sources are only activated when the translucent head plate [2] is pressed against the skin of the user, thereby preventing accidental turn on or light shining into the eye of the user.

Different light frequencies, or no light at all, may be optimal for different applicator discs [5] and/or disc covers [6]. Input from a sensor and/or switch may be applied to select the frequency of lights emitted by the light sources [23]. A sensor or switch may detect the type of applicator disc [5] and/or disc cover [6] attached to the housing [1], which may trigger a selected frequency of light emitted by the light sources [23]. For instance, a sensor may detect applicator discs and/or disc covers of selected colors, each of which may be assigned to a selected frequency of light. As another example, wherein the applicator disc may be attachable to the device via insertion plugs of selected shapes or lengths, a switch may detect the selected shape or length of applicator disc insertion plug, which may be assigned to a selected frequency of light. In this manner, interchangeable applicator discs [5] and/or disc covers [6] may activate different frequencies of light, or no light at all.

A timer [22] may be operatively coupled to the LEDs [23] such that light is applied for a prescribed amount of time.

The panel [3] or housing [1] of the device may additionally comprise a sonic emitter such as an ultrasonic transducer that produces ultrasonic sound that may be transmitted through apertures in the translucent head plate [2]. The motor may rotate, vibrate, or otherwise move to stimulate the skin.

A switch [10] may be included on the housing of the device to turn the device on and off, and a power source [12] may be included in or on the housing of the device to provide power. Various power sources such as batteries or DC power can be implemented. Batteries may be rechargeable or chargeable through electrical induction or through a port and cable connecting the device to a power source.

The invention claimed is:

1. A light treatment device comprising a housing having a transparent or translucent head plate integral with the housing; a panel with one or more light sources, wherein the panel is secured within the housing behind the transparent or translucent head plate whereby the one or more light sources shine through the head plate; and an applicator disc attachable to the device over the head plate, wherein the applicator disc comprises a base of one or more transparent or translucent sections whereby the one or more light sources shine through the head plate and the base of the applicator disc.

2. The light treatment device of claim 1 wherein the applicator disc is operatively coupled to a motor secured within the housing whereby the applicator disc is operable to rotate while the one or more light sources remains fixed.

3. The light treatment device of claim 1 wherein the device is operable to dispense an ingredient through the head plate and the applicator disc.

4. The light treatment device of claim 2 wherein the device is operable to dispense an ingredient through the head plate and the applicator disc.

5. The light treatment device of claim 1 further comprising a disc cover attachable to the applicator disc, wherein the disc cover comprises a base of one or more transparent or translucent sections whereby the one or more light sources shine through the head plate, the base of the applicator disc and the disc cover.

6. The light treatment device of claim 2 further comprising a disc cover attachable to the applicator disc, wherein the disc cover comprises a base of one or more transparent or translucent sections whereby the one or more light sources shine through the head plate, the base of the applicator disc and the disc cover.

7. The light treatment device of claim 3 further comprising a disc cover attachable to the applicator disc, wherein the disc cover comprises a base of one or more transparent or translucent sections whereby the one or more light sources shine through the head plate, the base of the applicator disc and the disc cover.

8. The light treatment device of claim 4 further comprising a disc cover attachable to the applicator disc, wherein the disc cover comprises a base of one or more transparent or translucent sections whereby the one or more light sources shine through the head plate, the base of the applicator disc and the disc cover.

9. The light treatment device of claim 1 wherein the one or more light sources are programmable to shine a first selected light frequency when a first applicator disc is attached to the device, and to shine a second selected light frequency when a second applicator disc is attached to the device.

10. The light treatment device of claim 2 wherein the one or more light sources are programmable to shine a first selected light frequency when a first applicator disc is attached to the device, and to shine a second selected light frequency when a second applicator disc is attached to the device.

11. The light treatment device of claim 3 wherein the one or more light sources are programmable to shine a first selected light frequency when a first applicator disc is attached to the device, and to shine a second selected light frequency when a second applicator disc is attached to the device.

12. The light treatment device of claim 4 wherein the one or more light sources are programmable to shine a first selected light frequency when a first applicator disc is attached to the device, and to shine a second selected light frequency when a second applicator disc is attached to the device.

13. A light treatment device comprising a housing having a transparent or translucent head plate integral with the housing; a panel with one or more light sources, wherein the panel is secured within the housing behind the transparent or translucent head plate whereby the one or more light sources shine through the head plate; and an applicator attachment attachable to the device surrounding the head plate, wherein the applicator attachment is operable to rotate around the head plate which remains fixed; and wherein the applicator attachment is further configured to dispense an ingredient to a skin of a user.

14. The light treatment device of claim 9 wherein the device is operable to dispense an ingredient through the head plate and/or the applicator attachment.

15. A light treatment device comprising a housing having a transparent or translucent head plate integral with the housing; and a panel with one or more light sources, wherein the panel is secured within the housing behind the transparent or translucent head plate whereby the one or more light sources shine through the head plate; wherein the device is operable to dispense an ingredient through the transparent or translucent head plate.

16. The light treatment device of claim 15 wherein the one or more light sources are programmable to shine a first selected light frequency when a first applicator disc is attached to the device, and to shine a second selected light frequency when a second applicator disc is attached to the device.

* * * * *